United States Patent
Conte

(10) Patent No.: US 10,246,819 B2
(45) Date of Patent: *Apr. 2, 2019

(54) COMPOSITIONS AND METHODS FOR REVERSIBLY DYEING SOFT CONTACT LENSES AND MEDICAL EXAMINATION THEREFROM

(71) Applicant: Michael D. Conte, Lake Worth, TX (US)

(72) Inventor: Michael D. Conte, Lake Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/809,544

(22) Filed: Nov. 10, 2017

(65) Prior Publication Data

US 2018/0100268 A1 Apr. 12, 2018

Related U.S. Application Data

(63) Continuation of application No. 15/291,469, filed on Oct. 12, 2016, now abandoned.

(51) Int. Cl.
| | | |
|---|---|---|
| *D06P 1/00* | (2006.01) | |
| *G02C 7/04* | (2006.01) | |
| *A61B 3/10* | (2006.01) | |
| *D06P 5/13* | (2006.01) | |

(52) U.S. Cl.
CPC .............. *D06P 1/0012* (2013.01); *A61B 3/10* (2013.01); *D06P 1/0016* (2013.01); *D06P 5/13* (2013.01); *D06P 5/138* (2013.01); *G02C 7/046* (2013.01)

(58) Field of Classification Search
CPC ........ D06P 1/0012; D06P 1/0016; D06P 5/13; D06P 5/138; A61B 3/10; G02C 7/049
See application file for complete search history.

(56) References Cited

U.S. PATENT DOCUMENTS

| | | | |
|---|---|---|---|
| 4,518,579 A | 5/1985 | Holly | |
| 4,842,401 A | 6/1989 | Maurice | |
| 6,218,428 B1* | 4/2001 | Chynn | A61K 9/0048 514/459 |
| 8,702,816 B2* | 4/2014 | Conte | B29D 11/00903 250/492.1 |
| 2004/0063591 A1* | 4/2004 | Borazjani | A01N 33/12 510/112 |
| 2007/0204411 A1* | 9/2007 | Conte | B29D 11/00317 8/507 |
| 2012/0091368 A1* | 4/2012 | Conte | B29D 11/00903 250/492.1 |

FOREIGN PATENT DOCUMENTS

CN 105031705 11/2015

OTHER PUBLICATIONS

White "Fluorescein Photography and the Evaluation of Cornea-to-Contact Lens Patterns in Patients with Different Severity Levels of Keratoconus" 2009.*

* cited by examiner

*Primary Examiner* — Amina S Khan
(74) *Attorney, Agent, or Firm* — Layman H. Moulton, Esq.; Moulton Patents, PLLC

(57) ABSTRACT

A composition, method and kit for producing reversibly dyed soft contact lenses is disclosed. The contact lenses are submerged in saline solution and a dye is added to the saline solution, either directly or by means of a strip that has been impregnated with the dye. After a period of time, the lens absorbs the dye and can be removed from the solution and placed on the eye. Once the lens is illuminated with ultraviolet light, it will glow or fluoresce. An eye having the soft contact lens applied to a cornea thereof is examined under a luminescent radiation stored in the soft contact lens. The dyeing method does not utilize heat and thus is reversible. Soaking the lens in additional saline solution for a period of time will cause the dye to return to its non-dyed state. A stabilizing compound and a method of stabilization are also disclosed herein.

4 Claims, 4 Drawing Sheets

COMPOSITIONS AND METHODS FOR REVERSIBLY DYEING SOFT CONTACT LENSES AND MEDICAL EXAMINATION THEREFROM

CROSS-REFERENCE TO RELATED APPLICATION

This application is a divisional of and claims the benefit of the priority date of earlier filed U.S. patent application Ser. No. 15/291,469, under the same title and filed Oct. 12, 2016 by Michael D. Conte, now abandoned, and is incorporated herein by reference in its entirety.

BACKGROUND AND FIELD OF INVENTION

One aspect of this invention pertains to colored, or dyed, hydrogel or silicon hydrogel substrate, and more particularly to compositions and methods for reversibly dyeing soft contact lenses.

Colored contact lenses have been steadily gaining in popularity amongst individuals who want to change their eye color or add a dramatic new feature to their appearance. Contact lens makers first started adding color to contact lens in the 1970s to make the lenses easier to see. The amount of pigment used to create this "handling tint" is so slight that it has essentially no effect on how the lens looks on the eye. By the 1980s, iris-altering contacts had been created. Some offered subtle changes, such as lenses that made blue eyes look bluer. Other, novelty lenses became available that could change the eye's appearance dramatically, such as by turning the iris a blood-red color, for instance, or making it look like a cat's eye.

The simplest colored lenses are enhancing lenses, which look like a regular contact lens with an iris-sized circle of transparent color. These lenses aren't meant to hide the iris's natural color, but rather to augment it. Manufacturers create the color by covalently attaching organic azo dyes to the contact lens polymer. The use of opaque pigments is more difficult, as it has a tendency to look fake. Colored contact makers have gotten better at making dramatic yet realistic-looking changes to the appearance of the iris through the use of sophisticated designs of opaque inorganic pigments. Nano- and microscale particles of inorganic pigments such as titanium dioxide, iron oxide, and barium sulfate are typically used to achieve the opaque color in these lenses. The FDA has only approved a small number of pigments for use with contact lenses. It is also important that the pigment used have no effect on the morphology and overall mechanical properties of the lens.

For some lenses, inks are printed directly onto the lens and then covalently fixed onto the polymer surface. Other colored contact lenses are made by putting the inks into a mold and polymerizing the lens around these pigments, encapsulating the color within the contact. Others are made by stacking layers of dielectric films of alternating low and high refractive index. This, in combination with the films' precise nanoscale thickness, allows scientists to tailor the lens's reflective properties and therefore its color. The thin films are applied to the lens using plasma-enhanced chemical vapor deposition or ion-assisted deposition. The process creates a smooth surface on the lens that's imperceptible to the wearer. All of these processes are complicated and require precise application of pigments or films through the use of highly sensitive and technical machinery.

Colored contact lenses that have a dyed iris area and a light reflecting material on the concave surface of the lens are known. The reactive dyes are attached to the lens through the formation of a covalent bond between the lens material and the dye that is created after the lens is contacted with the dye for a sufficient amount of time. These dyes permanently stain the matrix of the contact lens.

Also known are colored contact lenses in which the color is applied by direct application of one or more vat dyes, by printing the color onto the surface of the lens, or by incorporating a pigment onto the contact lens surface. These contact lenses are also permanently colored.

What is needed, therefore, is a simple method and kit for coloring contact lenses that is reversible and not permanent.

SUMMARY OF THE INVENTION

One embodiment of the present invention relates generally to the field of a hydrogel or silicon hydrogel substrate. More particularly, it concerns a stabilizing compound and a method of stabilization thereof and examining a physiology of an eye having the soft contact lens applied to a cornea thereof. A method for applying dyes to the surface of a soft contact lens, as well as a kit containing the components for application of a dye to a soft contact lens are also included. The dye is applied in a manner to give a dye that is reversible, fadable, and removable in that it does not permanently stain the lens.

Generally, one aspect of the current invention pertains to a method for reversibly coloring a substrate, such as contact lenses, preferably soft contact lenses. The method can be carried out by a contact lens owner after purchase from a manufacturer. The contact lenses are placed in a preserved saline solution. Next, a strip that has been impregnated with a dye is added to the saline solution in which the lens is being stored. In order to ensure that the dyeing process is reversible, it is important that no heat be applied to the system while the lens is being dyed. After the lens has absorbed or adsorbed the dye, the lens can be inserted into the eye as it would normally be worn by the user. Exposure of the dyed lenses to ultraviolet light causes the lenses to glow. These particular dyes cause the contact lens to fluoresce under fluorescent light, creating a dramatic effect. The dyes do not permanently change the substrate contact lens. The dye does not print color into any part of the contact lens matrix. This effect of dyeing will fade over time by itself as the dye slowly leaches out of the matrix of the lens, or the dying effect can be reversed by soaking the lens in saline solution for an amount of time. A kit containing all of the components to produce such reversible dyed contact lenses is also described.

A further embodiment of the method(s) includes stabilizing the combined solution with boric acid and a soluble sodium chloride adapted to maintain the combination solution at the temperature during the amount of time at a pH of 7.2 plus or minus 0.2 with an isotonic adjustment between 290 to 320 mOsm/kg. The method also includes adding a bacteriostatic and a fungistasis component to the combined solution to keep *pseudomonas aeruginosa* and the like from growing in the fluorescein solution. The method additionally includes examining a pathology of an eye having the reversibly dyed contact lens applied to a cornea thereof, the examining performed under a luminescent radiation stored in the reversibly dyed contact lens.

Additionally, embodiments include reducing the concentration adapted to reverse the dyeing of the combination solution at the temperature during the amount of time for a pH from 7.0 to 7.4. Also, examining a physiology of an eye under the luminescent radiation in the soft contact lens applied to a cornea thereof and after a luminescent dye is reversed in the soft contact lens. The disclosure also includes D&C Yellow No. 8 as a color additive in or on the contact lenses.

Other aspects and advantages of embodiments of the disclosure will become apparent from the following detailed description, taken in conjunction with the accompanying drawing(s), illustrated by way of example of the principles of the disclosure.

Figure 1:
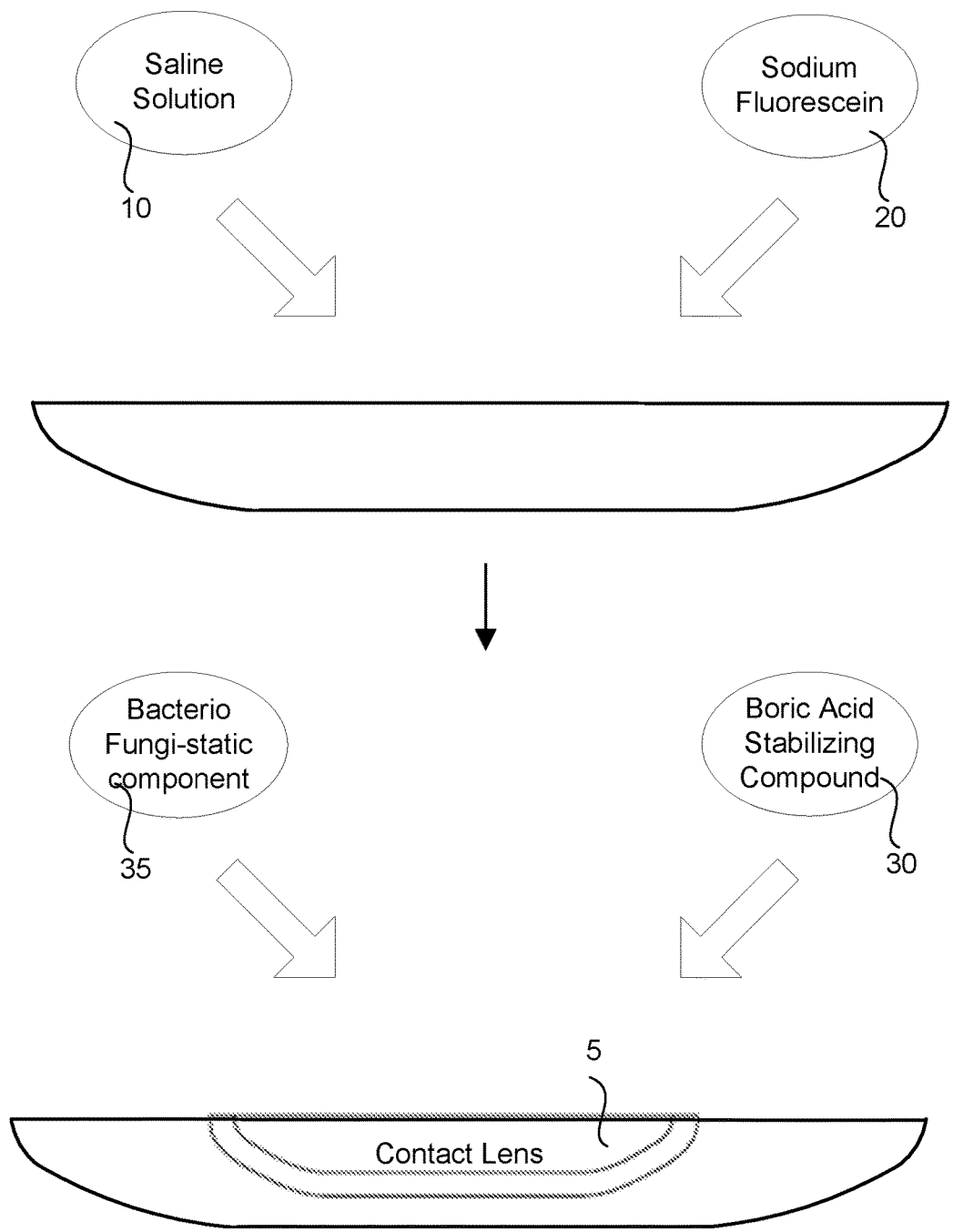
FIG. 1 is a depiction of a chemical composition for a stabilizing compound of the dye impregnated saline solution in accordance with an embodiment of the present disclosure.

Throughout the description, similar reference numbers may be used to identify similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

One embodiment of the present invention relates to methods and kits that utilize dyes to temporarily color the surface of hydrogel or silicon hydrogel substrate, such as a soft contact lens. The methods and kits produce contact lenses that will fluoresce or glow under fluorescent lights.

Soft contact lenses are also known as hydrogel and silicon hydrogel contact lenses. Soft contact lenses come in four (4) different groups. The first group is low water contact lenses containing less than fifty percent water and non-ionic hydrogel polymers. The second group is high water content lenses that contain over fifty percent water and non-ionic hydrogel polymers. The third group of soft contact lenses is low water contact lenses with less than fifty percent water and ionic hydrogel polymers. The fourth group is high water content lenses with greater than fifty percent water and ionic hydrogel polymers.

Generally, one aspect of the current application pertains to compositions and methods for reversibly dyeing soft contact lenses. The first step in the method comprises placing a soft contact lens in a container filled with saline solution. In the next step, a strip that has been impregnated with a dye is added to the saline solution that contains the soft contact lens, to produce a combination solution. After a period of time, the soft contact lens will absorb or adsorb the dye from the combination solution. Finally, the soft contact lens is removed from the combination solution, rinsed briefly with saline, and placed in the eye. Exposure to ultraviolet light will cause the soft contact lens to glow, especially in dim illumination or a dark room. This effect will fade over time as the dye slowly leaches out of the matrix of the lens, or the lens can be soaked in additional saline for a period of time to reverse the dyeing. The dyes do not permanently change the contact lenses. The dyes do not permanently stain the matrix of the contact lens.

Although many dyes can be used, the dyes for the current invention include sodium fluorescein, lissamine green, rose Bengal, and mixtures thereof. The most preferred dye is sodium fluorescein. The strips onto which the dyes can be absorbed include small paper strips about 2 mm wide and 15 mm long. The dyes can be absorbed or adsorbed by the strips by placing the absorbent paper strips in sodium fluorescein solution. In one embodiment, the strips absorb or adsorb up to about 30 milligrams of dye per strip. If the dye used is rose bengal, the amount of dye can be from about 1 milligram to about 20 milligrams. The amount of dye that is absorbed onto the strip may need to be increased depending on the amount of saline solution in the container. The usable amount of saline is up to about 10 milliliters but can be varied accordingly. An example of a commercially available sodium fluorescein strip is a FUL-GLO®, fluorescein sodium sterile ophthalmic strip (Buffalo Grove, Ill.). The strip preferably dissolves in the saline solution to produce a combination solution. The amount of time required for the contact lens to absorb the dye will vary, but the preferable minimum amount of time during which the contact lens should be left in the combination solution is about three hours.

In additional embodiments, the dye used is sodium fluorescein. The sodium fluorescein is added to the strip, or directly to the saline solution, in an amount of about 0.6 mg. The amount of sterile saline solution used is about 0.5 mL. The lens is placed into the saline solution containing the dye.

During the dyeing process, one range of temperature to maintain for the dye, the saline, and the lens is from about 62 to about 72 degrees Fahrenheit. The lens should be allowed to contact the dye and the saline for a period of at least about 6 hours and no longer than about 48 hours. In order to ensure that the dyeing process is reversible, the temperature of the dye, saline, and lens could be between about 45 and about 100 degrees Fahrenheit. In another embodiment, the temperature is in the range of from about 60 to about 82 degrees Fahrenheit. In yet another embodiment, the temperature preferably does not exceed 72 degrees Fahrenheit. Adding heat to the system will result in permanent dyeing that is not easily reversed. By avoiding the addition of heat, the dye does not form a permanent or covalent bond with the contact lens. If the dye is not permanently or covalently attached to the lens, then the dye can fade or be removed from the lens at a later time. The "reversible" dye on the lens can fade within about 48 hours at ambient temperature. The fading is accelerated at higher temperature.

In order to complete the reversing or removing of the dye process, the lens must be soaked in about 5 mL sterile saline solution for about 6 hours. This process should then be repeated twice more with new saline solution. After this, the lens should substantially return to its natural color.

In additional embodiments, the dye that is absorbed or adsorbed by the strip may be a mixture of any useable dyes.

One embodiment of the current invention also pertains to a kit that may be used to dye soft contact lenses. The kit contains four main components. The first component is a contact lens container. The container can be a 10 mL size contact lens cup holder or any other suitable container. The second component is a bottle of preserved saline solution, available from any commercial source. The third component is a strip that has been impregnated with a dye. The dye is preferably sodium fluorescein, lissamine green, or rose bengal. The strips may vary in size and may contain up to about 30 milligrams of dye per strip, depending on the size of the contact lens container and the selected dye. A fourth optional component is a UV light emitting system, such as a light bulb that emits ultraviolet light powered by a battery system.

To utilize the kit, the user deposits a contact lens, preferably a soft contact lens, into the contact lens container. The contact lens is one that has been prescribed by a doctor and obtained from a manufacturer of contact lenses. The container is then filled with saline solution from the bottle of preserved saline solution. The preferred amount of saline solution added is about 10 milliliters. A strip that has been impregnated with dye is then added to the saline solution. If the dye is sodium fluorescein, the strip should preferably contain up to about 30 milligrams of dye. The saline solution used can be up to about 10 milliliters. In some embodiments, about 0.6 mg sodium fluorescein is used in about 0.5 mL saline solution. The strip preferably dissolves in the saline solution to produce a combination solution containing molecules of dye. Alternatively, the dye is added directly to the saline solution, without the use of a strip. In both embodiments, the dye molecules are absorbed by the contact lens over a period of time. The contact lens should be left in the container with the combination solution for between about six hours and about 48 hours. No heat (i.e. the temperature of below about 100.degree. F.) should be applied to the system, rather, the temperature should be maintained between about 60 degrees and about 82 degrees Fahrenheit. A temperature of around 72 degrees F. has been found to work well. After the lenses are placed in the eye, the UV light emitting system should be permitted to shine into the eyes to cause the contact lenses to glow.

The effect of utilizing the kit to produce the dyed contact lenses is that the lenses will fluoresce or glow, especially in dim illumination or a dark room. This creates a dazzling, dramatic effect.

Another embodiment of the present invention pertains to producing a dyed contact lens, or enhancing the glow of a soft contact lens that has already been dyed, while the subject is wearing or using the contact lens. Here, from about 10 to about 20 volume percent of a dye in liquid tears (saline) in about 0.5 ml to about 2 ml single use packages is put directly on the eye with the soft contact lens to either dye the "un-dyed" contact lens or enhance the glowing of the contact lens that has already been dyed. Usable dyes include sodium fluorescein, lissamine green, rose Bengal, and mixtures thereof.

FIG. 1 is a depiction of a chemical composition for a stabilizing compound of the dye impregnated saline solution in accordance with an embodiment of the present disclosure. The depiction includes the soft contact lens 5, and the chemical composition includes a saline solution 10, and a sodium fluorescein dye 20 and the boric acid stabilizing compound 30 with claimed ingredients as explained and discussed herein. The combined solution also includes a bacteriostatic and a fungistasis component 35 adapted to keep *pseudomonas aeruginosa* and the like from growing in the fluorescein solution. The stabilizing compound 30 may be added prior to or after the contact lens 5 has been dyed. Additionally, the stabilizing compound may be added to one (left or right) contact lens and not to the other contact lens of a pair in order to have different luminescence from left to right in the contact lens pair.

A further embodiment of the method(s) includes stabilizing the combination solution via a stabilizing the combined solution with boric acid and a soluble sodium chloride adapted to maintain the combination solution at the temperature during the amount of time at a pH of 7.2 plus or minus 0.2 with an isotonic adjustment between 290 to 320 mOsm/kg.

Additionally, embodiments include reducing the concentration to reverse the dyeing of the combination solution at the temperature during the amount of time for a pH from 7.0 to 7.4.

Figure 2:
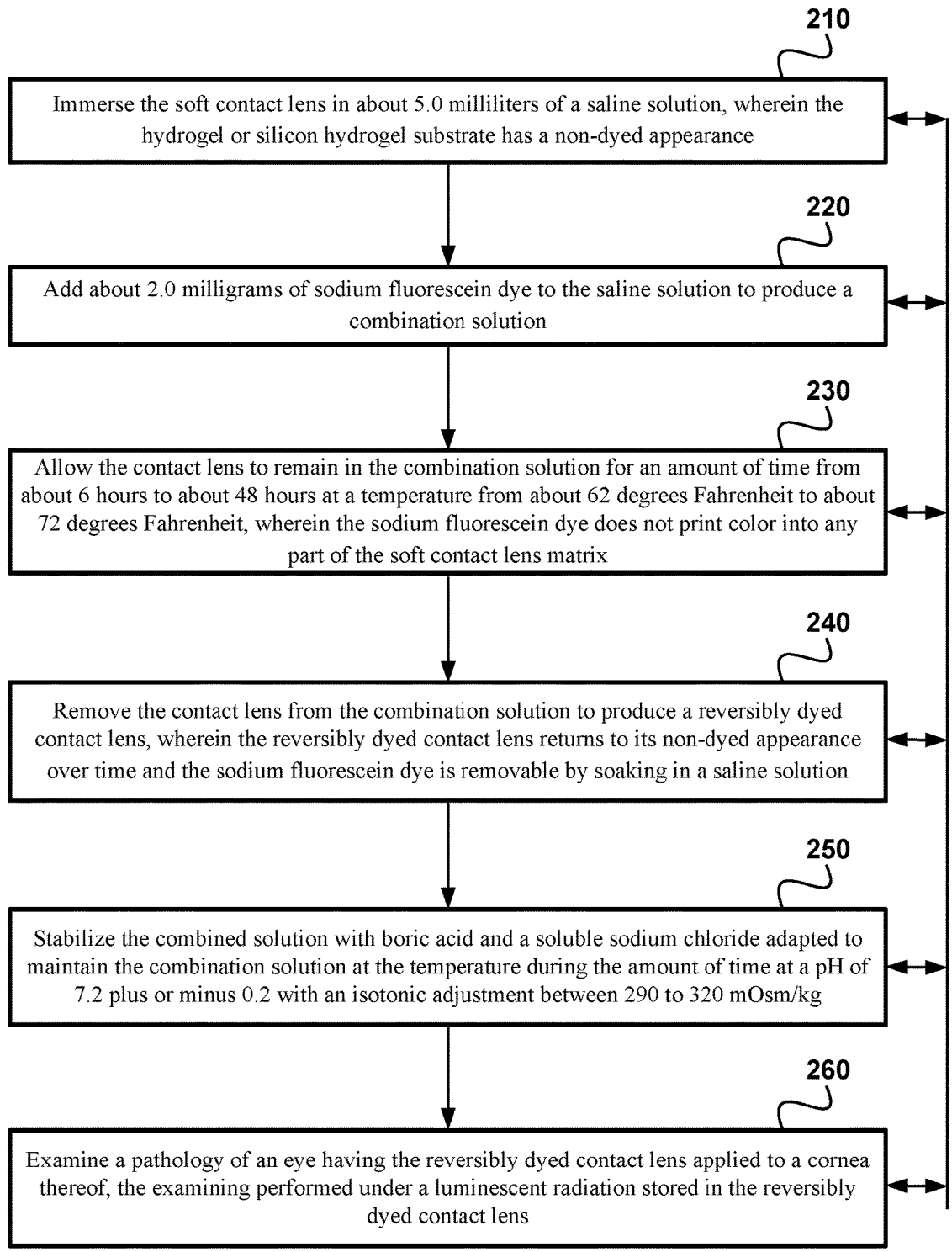
FIG. 2 is a block diagram of a method for stabilizing the dye impregnated saline solution (and the strip) in accordance with an embodiment of the present disclosure.

FIG. 2 is a block diagram of a method for stabilizing the dye impregnated saline solution (and the strip) in accordance with an embodiment of the present disclosure. The method includes 210 immersing the soft contact lens in about 0.5 milliliters of a saline solution, wherein the hydrogel or silicon hydrogel substrate has a non-dyed appearance. The method also includes 220 adding about 0.6 milligrams of sodium fluorescein dye to the saline solution to produce a combination solution. The method additionally includes 230 allowing the contact lens to remain in the combination solution for an amount of time from about 6 hours to about 48 hours at a temperature from about 62 degrees Fahrenheit to about 72 degrees Fahrenheit, wherein the sodium fluorescein dye does not print color into any part of the soft contact lens matrix. The method further includes removing 240 the contact lens from the combination solution to produce a reversibly dyed contact lens, wherein the reversibly dyed contact lens returns to its non-dyed appearance over time and the sodium fluorescein dye is removable by soaking in a saline solution. The method yet includes stabilizing 250 the combination solution with boric acid and a soluble sodium chloride adapted to maintain the combination solution at the temperature during the amount of time at a pH of 7.2 plus or minus 0.2 with an isotonic adjustment between 290 to 320 mOsm/kg. The method also includes adding a bacteriostatic and a fungistasis component to the combined solution to keep *pseudomonas aeruginosa* and the like from growing in the fluorescein solution. The method furthermore includes examining 260 a pathology of an eye having the reversibly dyed contact lens applied to a cornea thereof, the examining performed under a luminescent radiation stored in the reversibly dyed contact lens. An embodiment of the method disclosed may also include placing the contact lens on an eye and illuminating the eye with ultraviolet radiation configured to store luminescent radiation in the contact lens. Embodiments may further comprise adding the boric acid after the sodium chloride and the dye to adjust the pH of the combined solution to within 0.2 of 7.2.

Figure 3:
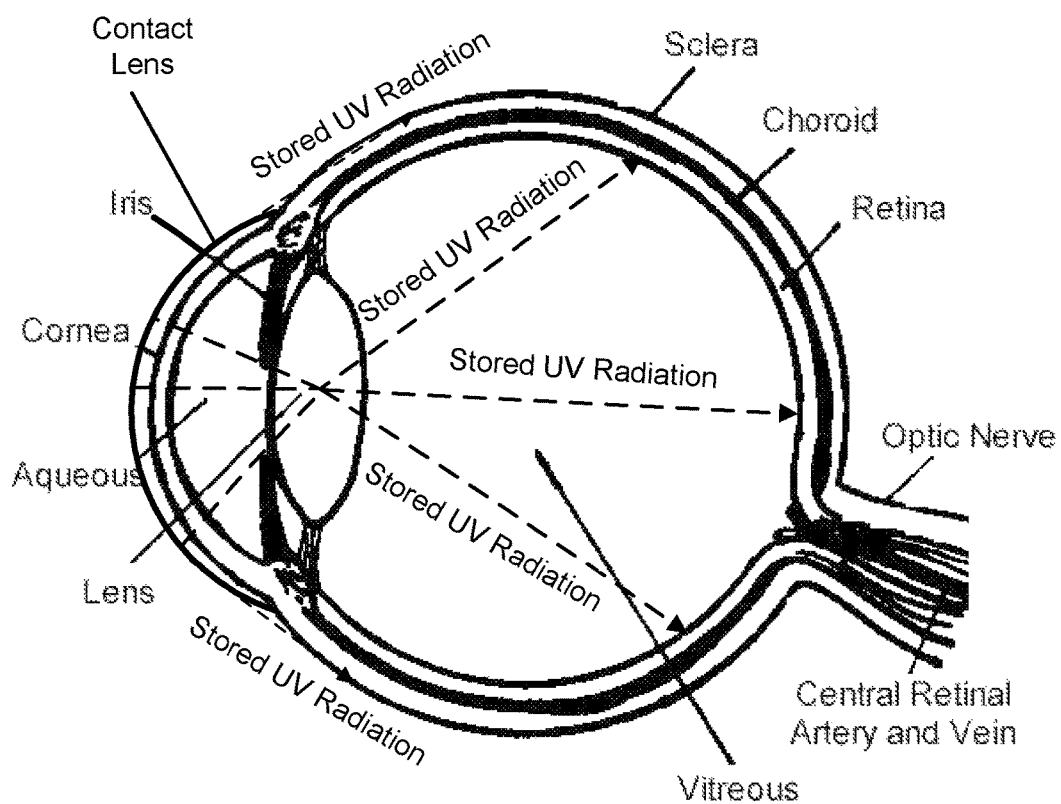
FIG. 3 is a depiction of a fluorescein impregnated contact lens which has been exposed to UV light and in turn radiates UV light immediately to surrounding tissue and tissue behind the lens of the human eye for medical examination and treatment in accordance with an embodiment of the present disclosure.

FIG. 3 is a depiction of a fluorescein impregnated contact lens which has been exposed to UV light and in turn radiates UV light immediately to surrounding tissue and tissue behind the lens of the human eye for medical examination and treatment. Benefits unknown to shining UV light remotely onto the eye are thus obtained. Since a soft contact lens may cover a large portion of the human cornea, the stored luminescent light therefrom enters the lens of the human eye radially from nearly 180 degrees as depicted in part by the broken lines in the drawing. This immediate coverage and exposure to luminescent light allows a broader interior illumination of the retina of the human eye for examination and treatment purposes without any dye solution in the eye. The broader illumination also of surrounding tissues including the iris and lens and sclera of the eye also allows for an extensive examination of the surrounding tissues under an ambient lighting therefrom. The stabilization of the dye in the contact lens also allows for a longer examination and treatment window with the benefits of UV light. Also, because the contact lens is reversibly dyed, controlled before and after dye experiments may be performed using the same contact lens for complete process control of experimental variables without any dye solution in the eye.

Figure 4:
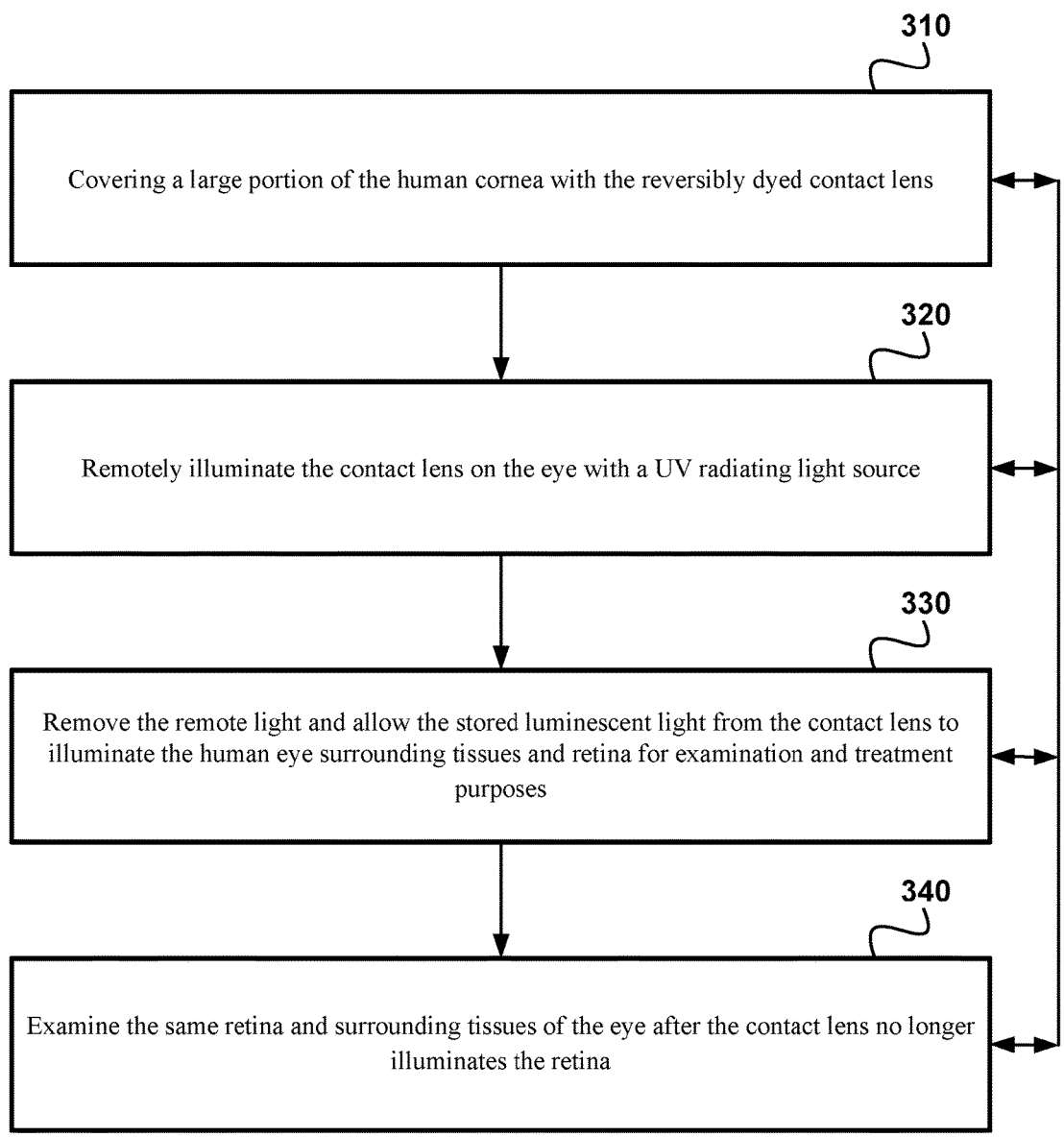
FIG. 4 is a block diagram of a method for examining the physiology of an eye having an illuminated contact lens fitted thereto in accordance with an embodiment of the present disclosure.

FIG. 4 is a block diagram of a method for examining the physiology of an eye having an illuminated contact lens fitted thereto in accordance with an embodiment of the present disclosure. In addition to the steps of the method included and discussed in regards to FIG. 2 above, the method includes 310 covering a large portion of the human cornea with the reversibly dyed contact lens. The method also includes 320 remotely illuminating the contact lens on the eye with a UV radiating light source. The method additionally includes 330 removing the remote light source and allowing the stored luminescent light from the contact lens to illuminate the human eye surrounding tissues and retina for examination and treatment purposes. The method further includes 340 examining the same retina and surrounding tissues of the eye after the contact lens no longer illuminates the retina. The broader illumination of surrounding tissues including the iris and lens of the eye allows for an extensive examination of the surrounding tissues under an ambient lighting therefrom.

An embodiment of the present disclosure may include 5 milliliters (ml) of purified water, 2 milligrams (mg) of fluorescein sodium, 45 mg of sodium chloride, and 5 mg of boric acid. The pH of the combined solution is a nominal 7.2 plus or minus 0.2. The combination solution also has an isotonic adjustment of between 290 to 320 mOsm/kg (osmality per killigram) at room temperature. The osmolality is measured in milliosmols (one-thousandth of an osmole) per kilogram of water (mOsmol/kg). Osmolarity is similar but is defined as the number of osmoles (or mOsmol) per liter of solvent and molarity (M) is equal to the number of moles of solute that are dissolved per Liter of solvent. There is a final filtration of the combined solution through sterile 0.2 um filters. The QS (quantity sufficient) requires adding enough solvent to bring the total volume of the combination solution to 5.0 milliliters. Weights are drying ingredients for a 0.04% weight per volume Fluorescein sodium, 0.9% sodium chloride, and 0.1% boric acid. The sodium chloride is first added to the purified water, the fluorescein sodium is next added and the boric acid is added thereto. More specifically the sodium chloride may comprise UNII: 451W47IQ8X and the sodium cation UNII: LYR4M0NH37 per the USP-NF. The United States Pharmacopeia and The National Formulary (USP-NF) is a book of public pharmacopeial standards for chemical and biological drug substances, dosage forms, compounded preparations, excipients, medical devices, and dietary supplements. The purified water may comprise UNII: 059QF0KO0R and the boric acid may comprise UNII: R57ZHV85D4.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

While the forgoing examples are illustrative of the principles of the present disclosure in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the disclosure be limited, except as by the specification and claims set forth herein.

What is claimed is:

1. A method for examining an eye via a hydrogel or silicon hydrogel substrate, comprising:
   a) immersing a hydrogel or silicon hydrogel substrate in a saline solution outside the eye, wherein the hydrogel or silicon hydrogel substrate has a non-dyed appearance, wherein the hydrogel or silicon hydrogel substrate is a soft contact lens;
   b) adding a dye to the saline solution to produce a combination solution;
   c) allowing the hydrogel or silicon hydrogel substrate to remain in the combination solution for an amount of time at a temperature from about 60.degree. F. to about 82.degree. F., wherein the dye does not print color into any part of the soft contact lens matrix; and
   d) examining the internal and external pathology of an eye by placing on the cornea of the eye the reversibly dyed contact lens and illuminating the inside and the outside of the eye with ultraviolet radiation, removing the ultraviolet radiation and examining the retina, sclera and surrounding tissues of the eye for a corneal abrasion or for a small particle in the eye via a luminescent radiation stored only in the contact lens.

2. The method of claim 1, further comprising stabilizing the combined solution with boric acid and a soluble sodium chloride adapted to maintain the combination solution at the temperature during the amount of time at a pH of 7.2 plus or minus 0.2 with an isotonic adjustment between 290 to 320 mOsm/kg.

3. The method of claim 1, further comprising adding a bacteriostatic and a fungistatic component to the combined solution to keep *pseudomonas aeruginosa* from growing in the combined solution.

4. The method of claim 1, further comprising examining a retina and surrounding tissues of the eye under ambient lighting from the surrounding tissues of the eye after the contact lens is removed and no longer illuminates the retina.

* * * * *